(12) United States Patent
Nisoli et al.

(10) Patent No.: US 6,315,868 B1
(45) Date of Patent: Nov. 13, 2001

(54) METHOD OF SEPARATING DIMETHYL CARBONATE AND METHANOL

(75) Inventors: Alberto Nisoli, Niskayuna, NY (US); Stephan Mathijs Bouwens, Bergen op Zoom (NL); Michael Francis Doherty, Montague; Michael Francis Malone, Amherst, both of MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/296,186

(22) Filed: Apr. 26, 1999

(51) Int. Cl.[7] .............................. B01D 3/40; C07C 27/32; C07C 69/96
(52) U.S. Cl. ................................ 203/57; 203/60; 203/63; 203/64; 203/65; 203/99; 203/DIG. 19; 203/DIG. 23; 558/277; 568/913
(58) Field of Search .................................. 203/65, 63, 60, 203/57, 99, 64, DIG. 19, DIG. 23; 558/274, 277; 568/913

(56) References Cited

U.S. PATENT DOCUMENTS 4,162,200 * 7/1979 Himmele et al. ...................... 203/58
4,310,388 * 1/1982 Volkamer et al. ...................... 203/51
5,292,917 * 3/1994 Nishihira et al. ...................... 558/277
5,426,207 * 6/1995 Harrison et al. ...................... 558/274

FOREIGN PATENT DOCUMENTS

| 581115A2 | 2/1994 | (EP) . |
| 6016596 | 1/1994 | (JP) . |
| 6228026 | 8/1994 | (JP) . |

OTHER PUBLICATIONS

Patent Abstracts of Japan, vol. 018, No. 222 (C–1193), Apr. 21, 1994.
Chemical Abstracts, vol. 130, No. 1, Jan. 4, 1999.
CN 1 212 172 A (China Petrochemical Corp.) Mar. 31, 1999, Chemical Abstracts, vol. 133, No. 1.

* cited by examiner

Primary Examiner—Virginia Manoharan
(74) Attorney, Agent, or Firm—Andrew J. Caruso; Donald S. Ingraham

(57) ABSTRACT

A method of separating methanol and dimethyl carbonate in a distillation column through extractive distillation. The extractive distillation is conducted in the presence of an extractive distillation agent which modifies the azeotropic behavior of the dimethyl carbonate/methanol mixture. A vapor side stream is removed from the distillation column.

12 Claims, 3 Drawing Sheets

METHOD OF SEPARATING DIMETHYL CARBONATE AND METHANOL

FIELD OF THE INVENTION

This invention relates to a method of separating dimethyl carbonate and methanol by extractive distillation. The extractive distillation is conducted in the presence of an extractive distillation agent which modifies the azeotropic behavior of the dimethyl carbonate/methanol mixture.

BACKGROUND OF THE INVENTION

Dimethyl carbonate is useful as a starting material in the synthesis of aromatic polycarbonates, as a solvent, and as a reactant in the production of a number of chemical products. Dimethyl carbonate is often present in a mixture with methanol. In various processes to produce dimethyl carbonate, for instance, dimethyl carbonate is obtained in a mixture with methanol. Dimethyl carbonate and methanol form an azeotropic composition having a weight ratio of dimethyl carbonate to methanol of about 30:70 at atmospheric pressure.

It is necessary, therefore, to separate the dimethyl carbonate from the dimethyl carbonate/methanol mixture. Processes used to separate the azeotropic mixture of dimethyl carbonate and methanol include pressure swing distillation, high pressure distillation and extractive distillation.

Extractive distillation is a method to separate components of a mixture that exhibits azeotropic behavior. In an extractive distillation process, an agent, herein referred to as an "extractive distillation agent" is added to mixture of components to be separated in the distillation process, so that the relative volatilities of the components of the mixture are changed. The change in relative volatilities is such that a sufficient difference in volatility of the components results, and effective separation by distillation becomes possible.

U.S. Pat. No. 5,292,917 discloses a process for the extractive distillation of a dimethyl carbonate/methanol mixture by distilling the mixture in the presence of dimethyl oxalate. Two distillation columns are used in series to separate the dimethyl carbonate from the methanol. In the first column, methanol is removed at the top of the column, and the dimethyl carbonate/dimethyl oxalate mixture is fed to the second column. In the second column, the dimethyl carbonate is separated from the dimethyl oxalate.

Japanese Publication 06228026, published on Aug. 16, 1994, discloses a method of extractive distillation of a mixture of methyl carbonate and methanol in the presence of an extractive agent selected from a group of compounds, including anisole.

Japanese Publication 06016596, published on Jan. 25, 1994, discloses a method of separating dimethyl carbonate from methanol by refluxing the dimethyl carbonate/methanol mixture in the presence of an organic solvent, e.g. phenol, and removing methanol as an overhead product and a mixture of the organic solvent and dimethyl carbonate as the bottom product.

Known methods for separating a dimethyl carbonate/methanol mixture involve at least two distillation columns. Therefore, there exists a need for a simplified and more economical process for separating a dimethyl carbonate/methanol mixture.

SUMMARY OF THE INVENTION

The present invention simplifies the process and provides further surprising properties. These and further properties of the invention will be more readily appreciated when considering the following disclosure and appended claims.

The present invention concerns a method of separating dimethyl carbonate and methanol from a mixture comprising dimethyl carbonate and methanol in a single distillation column, the method comprising the steps of:

A) distilling a mixture comprising dimethyl carbonate and methanol in the presence of an extractive distillation agent selected from the group consisting of an aromatic hydroxy compound, an alkyl aryl ether, a dialkyl carbonate, an alkyl aryl carbonate, a diaryl carbonate, an alkylene carbonate and an alicyclic alcohol; and B) removing a side stream comprising primarily dimethyl carbonate from the distillation column.

The invention further concerns a method for purifying dimethyl carbonate in a single distillation column comprising the steps of:

A) feeding a dimethyl carbonate/methanol feed stream comprising dimethyl carbonate and methanol and a second stream comprising an extractive distillation agent into the distillation column, the dimethyl carbonate/methanol feed stream being fed into the extractive distillation column below the second stream, the extractive distillation agent selected from the group consisting of an aromatic hydroxy compound, an alkyl aryl ether, a dialkyl carbonate, an alkyl aryl carbonate, a diaryl carbonate, an alkylene carbonate and an alicyclic alcohol;

B) distilling the dimethyl carbonate and methanol in the presence of the extractive distillation agent in the distillation column and;

C) removing an overhead product stream, a side product stream, and a bottom product stream from the distillation column, the overhead product stream comprising primarily methanol, the side product stream comprising primarily dimethyl carbonate and the bottom product stream comprising primarily the extractive distillation agent.

In the present invention, a side stream distillation column replaces two distillation columns, each having a reboiler and condenser. The side stream distillation column may be used with a side rectification column if a higher purity product is desired. In the embodiment where a side rectification column is used, the side rectification column is coupled to the side stream distillation column.

DETAILED DESCRIPTION OF THE INVENTION

Figure 1:
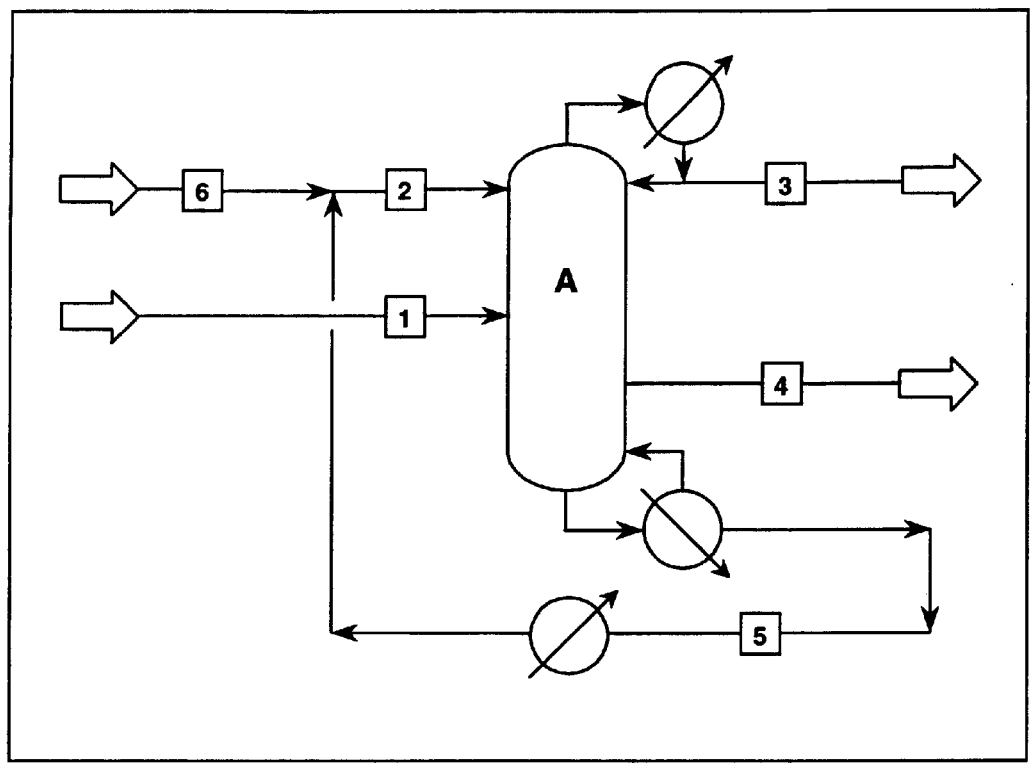
FIG. 1 is a schematic drawing showing one embodiment of the invention.

The present invention may be understood more readily by reference to the following detailed description of preferred embodiments of the invention and the examples included therein.

Before the present processes and compositions of matter are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings;

The singular forms "a", "an" and "the" include plural referents unless the context clearly dictates otherwise.

"Optional" or "optionally" means that the subsequently described event or circumstances may or may not occur, and that the description includes instances where the event occurs and instances where it does not.

"Comprising primarily" and "relatively pure" when used in reference to the composition of a stream entering or leaving the distillation column means that the referenced mixture comprises at least 85% by weight of the specified material.

"Pure" when used in reference to the composition of a stream entering or leaving a distillation column or rectification column means that the referenced mixture comprises at least 95% by weight of the specified material.

A "distillation column" as used herein refers to a column having a reboiler and a condenser.

A "side rectification column" as used herein refers to a column in which the energy input to the side rectification column is provided by a vapor side stream drawn from a distillation column. The side rectification column does not have a reboiler.

The present invention concerns a method or purifying dimethyl carbonate in a single distillation column comprising the steps of:

A) distilling a mixture comprising dimethyl carbonate and methanol in the presence of an extractive distillation agent selected from the group consisting of an aromatic hydroxy compound, an alkyl aryl ether, a dialkyl carbonate, an alkyl aryl carbonate, a diaryl carbonate, an alkylene carbonate and an alicyclic alcohol; and B) removing a side stream comprising primarily dimethyl carbonate from the distillation column.

In one embodiment, the invention concerns a method for purifying dimethyl carbonate in a single distillation column comprising the steps of:

A) feeding a dimethyl carbonate/methanol feed stream comprising dimethyl carbonate and methanol and a second stream comprising an extractive distillation agent into the distillation column, the dimethyl carbonate/methanol feed stream being fed into the distillation column below the second stream, the extractive distillation agent selected from the group consisting of an aromatic hydroxy compound, an alkyl aryl ether, a dialkyl carbonate, an alkyl aryl carbonate, a diaryl carbonate, an alkylene carbonate and an alicyclic alcohol;

B) distilling the dimethyl carbonate and methanol in the presence of the extractive distillation agent in the distillation column; and C) removing an overhead product stream, a side product stream, and a bottom product stream from the distillation column, the overhead product stream comprising primarily methanol, the side product stream comprising primarily dimethyl carbonate and the bottom product stream comprising primarily the extractive distillation agent.

It should be understood that the steps of the distillation process as defined are conducted simultaneously, and preferably, continuously.

The known process of separating dimethyl carbonate and methanol in an extractive distillation process involves more than one distillation column, each column having a reboiler and an overhead condenser. It was unexpectedly found that removal of a side stream comprising primarily dimethyl carbonate in an extractive distillation column obviates the need for a second distillation column having a reboiler and an overhead condenser thus greatly simplifying the process and reducing expense.

It has been unexpectedly found that removal of a stream comprising primarily dimethyl carbonate from the distillation column allows separation of three relatively pure product streams. By "comprising primarily" and "relatively pure" it is meant that the respective product streams comprise at least 85% by weight of methanol, dimethyl carbonate or the extractive distillation agent.

In the method of the invention, a side stream comprising primarily dimethyl carbonate is removed from the distillation column. The point of removal of the side stream is at or near a point in the column where the mass fraction of the dimethyl carbonate in the column is at a maximum. This point varies depending on the conditions of the column, such as pressure and number of stages. The point may be determined by an iterative process as described in Table 1 of "A Geometric Design Method for Side-Stream Distillation Columns"*Industrial & Engineering Chemistry Research*, Volume 35, Issue 10, pp. 3653–3664, or it may be determined using known computer simulation models, such as Aspen-Plus™ developed by Aspen Technology Inc., Cambridge, Mass., discussed further in the experimental portion of this specification.

The iterative process described in Table 1 of "A Geometric Design Method for Side-Stream Distillation Columns", *Industrial & Engineering Chemistry Research*, is as follows. In determining the location of the side stream for an upper side stream column: 1) the column pressure, flow rate, composition and enthalpy of the feed stream are first specified; 2) a distillate composition is chosen; 3) a reflux ratio is chosen, 4) the rectifying profile, the composition profile in the rectification section, is determined; 5) a side stream location on the rectifying profile is chosen; 6) a bottoms composition is chosen; 7) flows of the distillate, bottoms and side stream may be determined from this profile; 8) a middle profile is then determined followed by a determination of the stripping profile. If the middle and stripping profiles intersect the process is complete. If not, the reflux ratio or other specified value is adjusted and the process is repeated, beginning with step 2), the choice of distillate composition.

In determining the side stream for a lower side stream column, the process is the same, with the exception that the stripping profile is first determined, and the side stream position is chosen in the stripping profile rather than the rectifying profile.

The position of the side stream may be above or below the feed stream comprising the dimethyl carbonate/methanol mixture, herein referred to as the "dimethyl carbonate/methanol feed stream". If the side stream is above the dimethyl carbonate/methanol feed stream, the column is designated as an "upper side stream column", with the side stream between the feed stream and the distillate. If the side stream is below the dimethyl carbonate/methanol feed stream, the column is designated as a "lower side stream column". It is preferable to operate the process as a lower side stream column. It is also preferable that the side stream be a vapor side stream.

The configuration of the column, including the diameter, number of stages and feed points; and the operating parameters of the column, including the reflux ratio, temperature and pressure, typically vary depending on the desired purity of the product. The column is preferably operated at a pressure of from about 0.1 to 10 bar, more preferably 0.5 to 5 bar, even more preferably 1 to 3 bar. The boilup ratio at which the distillation column is maintained should be sufficiently high such that at one point in the column, the mass fraction of the dimethyl carbonate is at or near a maximum.

The number of theoretical stages in the column typically vary depending on a number of factors including the energy expenditure desired, available utilities, etc. Suitable numbers of theoretical stages for the distillation column include but are not limited to from 20 to 60, preferably 30 to 50 theoretical stages.

The extractive distillation agent used in the distillation is a compound that does not form an azeotrope with methanol or dimethyl carbonate, and which boils at a higher temperature than both methanol and dimethyl carbonate. The extractive distillation agent is selected from the group consisting of aromatic hydroxy compounds; alkyl aryl ethers; such as anisole, dialkyl carbonates; alkyl aryl carbonates; diaryl carbonates; alkylene carbonates and alicyclic alcohols. Aromatic hydroxyl compounds, such as phenol, are preferred. Phenol and anisole are more preferred extractive distillation agents; phenol is even more preferred.

The mass ratio of the second stream comprising the extractive distillation agent to the dimethyl carbonate/methanol feed stream fed into the column depends on the extractive agent used in the distillation. Suitable values for the mass ratio of the second stream to the first stream range from about 0.1:1 to about 10:1.

In the case of phenol, the mass ratio of the second stream comprising phenol to the dimethyl carbonate/methanol feed stream is about 2:1 to 4:1, more preferably 3:1. In the case of anisole, the mass ratio of the second stream comprising the anisole to the dimethyl carbonate/methanol feed stream is about 0.5:1 to 2:1, preferably 0.8:1 to 1:1.

It is preferable that the extractive distillation agent fed into the distillation column be pure, in particular, it is preferred that the second stream comprising the extractive distillation agent comprises preferably 95% or greater, even more preferably 99% or greater by weight of the extractive distillation agent.

The composition of the dimethyl carbonate/methanol feed stream fed into the column varies depending on the source of the stream. The dimethyl carbonate/methanol feed stream preferably comprises from 20 to 30% by weight of dimethyl carbonate; the composition at which the dimethyl carbonate/methanol mixture is at or near its azeotrope at atmospheric pressure is the most preferred.

The molar reflux ratio and the molar boilup ratio may be varied depending on a variety of factors including the number of stages in the column, desired product purity, particular extractive distillation agent, etc., and may be easily determined by the skilled worker. Suitable values for the molar reflux ratio for a distillation column in which anisole is used as the extractive distillation agent, include but are not limited to molar reflux ratios in the range from about 1 to 5, more preferably 1.2 to 2; suitable values for the molar reflux ratio in which phenol is used as an extractive distillation agent, include but are not limited to molar reflux ratios in the range of from about 0.5 to 2, preferably 0.5 to 1.0.

Suitable values for the molar boilup ratio for a distillation column in which anisole is used as the extractive distillation agent, include but are not limited to molar boilup ratios in the range of about 5 to 8, preferably about 6 to 7; suitable values for the molar boilup ratio in which phenol is used as the extractive distillation agent, include but are not limited to molar boilup ratios in the range from about 1 to 2, preferably about 1.5 to about 1.7.

Optionally, the stream comprising primarily dimethyl carbonate leaving the first distillation column may be further purified. In one embodiment of the invention, the stream comprising primarily dimethyl carbonate leaving the first column may be fed into a side rectification column. The number of stages in the side rectification column may be varied depending on the desired purity. It is preferable that the side rectification column contain from about 3 to about 10 theoretical stages.

Referring to FIG. 1, an embodiment of the invention is shown schematically. The dimethyl carbonate/methanol feed stream 1 comprises a mixture of methanol and dimethyl carbonate, second stream 2 comprises the extractive distillation agent. Streams 1 and 2 are fed continuously to the side stream distillation column A. Stream 3 is the overhead product and comprises primarily methanol. The purity will depend on the reflux ratio and the amount of extractive distillation agent fed to the column. Stream 4 is the side stream and comprises primarily dimethyl carbonate. The purity of stream 4 depends on the number of stages and the boilup ratio of the column. Stream 5 is the bottom product and comprises primarily the extractive distillation agent which is cooled and recycled back to the upper feed of the column (stream 2). Stream 6 is an extractive distillation agent makeup stream to account for the extractive distillation agent loss in the side stream.

Figure 2:
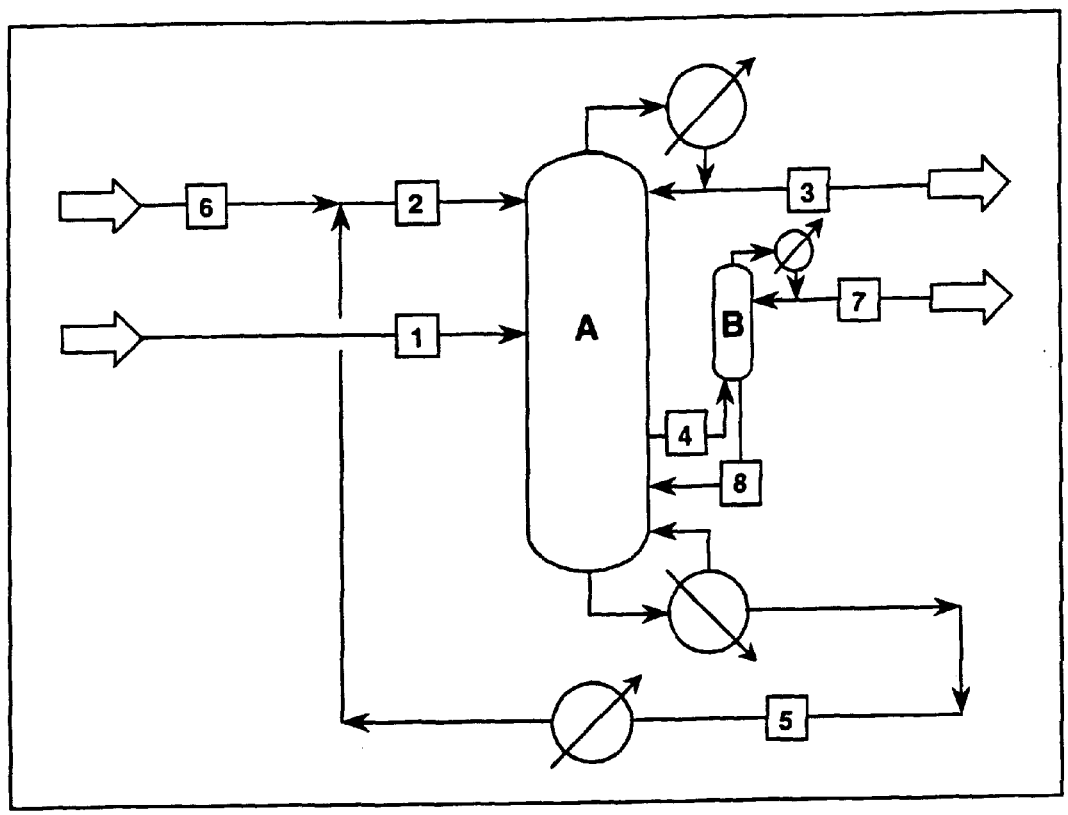
FIG. 2 is a schematic showing an embodiment of the invention having a side rectification column.

Referring to FIG. 2, a further embodiment of the invention is shown schematically. In this embodiment, stream 4 is fed to the side rectification column B, which comprises a column with a condenser, but no reboiler since the feed to the rectifier is the vapor side stream from the main column A. The pure dimethyl carbonate is removed in stream 7, while the bottom liquid stream from the side rectifier, stream 8, is sent back to the extractive distillation Column A at the same stage of stream 4 or below.

Figure 3:
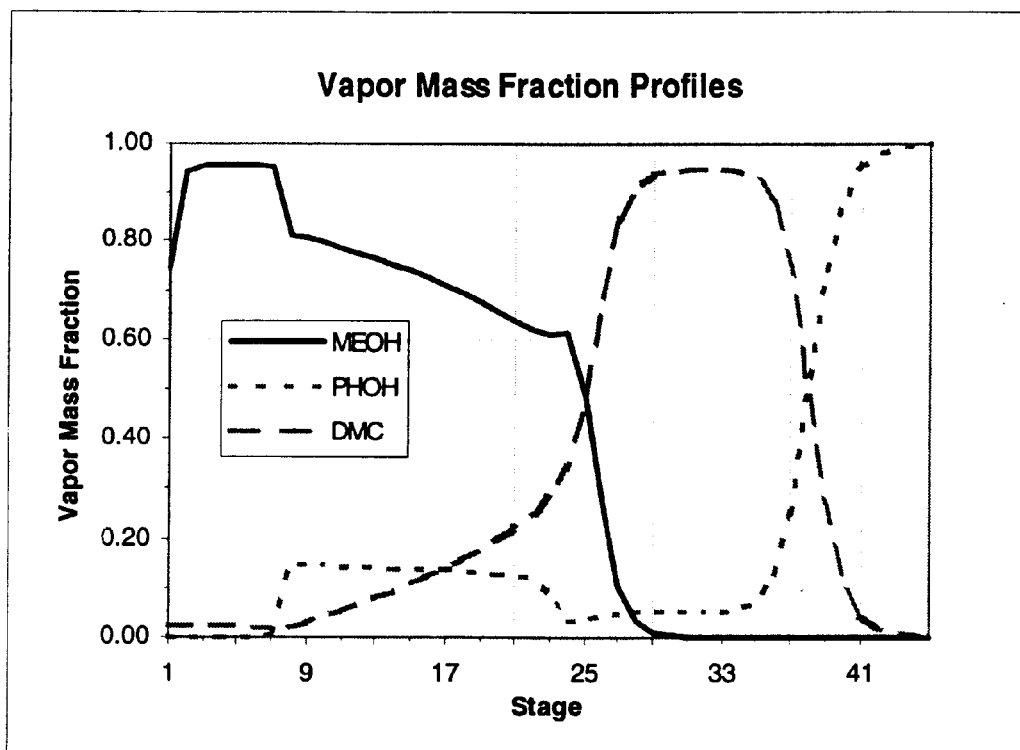
FIG. 3 is a graph in which the vapor mass fractions of the components are plotted versus the number of theoretical stages in the column.

Referring to FIG. 3, a graph showing the vapor mass fraction of the components in column A versus the number of theoretical stages is set forth. This graph is relative to the simulation described in Example 1. Only the main components (methanol, dimethyl carbonate and phenol) are plotted; for this reason the sum of the vapor mass fractions shown in the graph does not close to 1 at stage 1 (the light impurities have been omitted from the graph). The vapor side stream is preferably removed at a point at or near the maximum in the dimethyl carbonate profile.

EXAMPLES

The following examples are put forth so as to provide with a complete disclosure and description of how the method claimed herein is practiced, and is not intended to limit the scope of what the inventors regard as their invention. Efforts have been made to ensure accuracy with respect to numbers (e.g., amounts, temperature, etc.). Unless indicated otherwise, parts are by weight, temperature is in ° C. and pressure is in bar.

The following data were generated using the software AspenPlus™ developed by Aspen Technology Inc., Cambridge, Mass. For the multi-component systems including methanol, dimethyl carbonate, phenol, and anisole, the NRTL-RK physical property option set was chosen (liquid phase modeled using NRTL activity coefficients, vapor phase modeled using the Redlich-Kwong equation of state). NRTL binary parameters for the binary pairs including the above components were regressed from proprietary vapor liquid experimental data.

To obtain the position of the side stream, several simulations were run with different side stream positions and the best case was retained. Without wishing to be bound by any theory or explanation, it is believed that the ASPEN PLUS program can sufficiently predict the behavior of the three component system as described herein. The streams and columns referred to in the following Examples are labeled in accordance with FIGS. 1 and 2.

In the examples below, the dimethyl carbonate/methanol feed stream contains light impurities that are expected to leave the system with the methanol product stream (stream 3). "Light impurities" include, but are not limited to methylal, dimethyl ether, methyl chloride, CO, $CO_2$ and water which result from the process to make DMC from methanol, CO and oxygen.

Example 1

In this example, column A is a column having 45 theoretical stages, including reboiler and condenser. The extractive distillation agent is phenol. Numbered from the top, the condenser is stage 1. The dimethyl carbonate/methanol feed stream, stream 1 is introduced at stage 24, the extractive distillation feed, stream 2, is introduced at stage 8, and the side stream, steam 4, is removed at stage 33. The top pressure of the column is 2.9 bar, the molar reflux ratio is 0.6 and the molar boilup ratio is 1.63.

Column B is a column having 4 theoretical stages, including the condenser. The top pressure is atmospheric, the molar reflux ratio is 0.32 and the mass ratio of the distillate to the feed is 0.92.

The results of this simulation are set forth in Table I.

Example 3

In this example, column A is a column having 45 theoretical stages, including reboiler and condenser. The extractive distillation agent is anisole. Numbered from the top, the condenser is stage 1. The dimethyl carbonate/methanol feed stream, stream 1, is introduced at stage 24, the extractive distillation feed, stream 2, is introduced at stage 10, the side stream, steam 4, is removed at stage 30. The top pressure of

TABLE I

| | Stream | | | | | | | |
|---|---|---|---|---|---|---|---|---|
| Phase | 1 LIQUID | 2 LIQUID | 3 LIQUID | 4 VAPOR | 5 LIQUID | 6 LIQUID | 7 LIQUID | 8 LIQUID |
| Mass Flow KG/HR | | | | | | | | |
| $CO_2$ | 78.0 | — | 78.0 | — | — | — | — | — |
| MEOH | 20019.6 | — | 20019.2 | 0.4 | — | — | 0.4 | 0.0 |
| PHOH | — | 100000.0 | — | 433.1 | 99964.1 | 35.9 | 35.9 | 397.2 |
| DMC | 7782.9 | 20.0 | 513.5 | 7566.2 | 20.0 | — | 7269.4 | 296.9 |
| $H_2O$ | 1.0 | — | 0.8 | 0.2 | — | — | 0.2 | 0.0 |
| DME | 50.6 | — | 50.6 | — | — | — | — | — |
| METHYLAL | 497.9 | — | 497.9 | 0.0 | — | — | 0.0 | — |
| MECL | 71.1 | — | 71.1 | — | — | — | — | — |
| CO | 0.5 | — | 0.5 | — | — | — | — | — |
| Mass Flow KG/HR | 28502 | 100020 | 21232 | 8000 | 99984 | 36 | 7306 | 694 |
| Volume Flow CUM/HR | 35.43 | 96.96 | 28.13 | 1026.01 | 113.06 | 0.04 | 8.01 | 0.74 |
| Density KG/CUM | 805 | 1032 | 755 | 7.80 | 884 | 1032 | 912 | 939 |
| Temperature C | 65.2 | 79.9 | 66.0 | 152.3 | 225.3 | 80.0 | 90.4 | 123.6 |
| Pressure BAR | 6.00 | 4.00 | 2.86 | 2.91 | 2.93 | 3.00 | 1.01 | 3.04 |

Example 2

In this example, the configuration of column A is the same as in example 1. The extractive distillation agent is phenol. The top pressure is 1.5 bar, the molar reflux ratio is 0.80 and the molar boilup ratio is 1.55.

Column B is a column having 4 theoretical stages, including condenser. The top pressure is atmospheric, the molar reflux ratio is 0.30 and the mass ratio of distillate to feed is 0.90.

The results of this simulation are set forth in Table II.

the column is 2.9 bar. The molar reflux ratio is 1.50 and the molar boilup ratio is 6.56.

Column B is a column having 6 theoretical stages. The top pressure is 1 atm. The molar reflux ratio is 0.23 and the mass ratio of the distillate to the feed is 0.90.

The results of this simulation are set forth in Table III.

TABLE II

| | Stream | | | | | | | |
|---|---|---|---|---|---|---|---|---|
| Phase | 1 LIQUID | 2 LIQUID | 3 LIQUID | 4 VAPOR | 5 LIQUID | 6 LIQUID | 7 LIQUID | 8 LIQUID |
| Mass Flow KG/HR | | | | | | | | |
| $CO_2$ | 78.0 | — | 78.0 | — | — | — | — | — |
| MEOH | 20019.6 | — | 20002.5 | 17.3 | — | — | 17.1 | 0.2 |
| PHOH | — | 100000.0 | — | 473.6 | 99982.1 | 17.9 | 17.9 | 455.7 |
| DMC | 7782.9 | 1.0 | 664.8 | 7508.3 | 1.0 | — | 7118.1 | 390.2 |
| $H_2O$ | 1.0 | — | 0.2 | 0.8 | — | — | 0.8 | 0.0 |
| DME | 50.6 | — | 50.6 | — | — | — | — | — |
| METHYLAL | 497.9 | — | 497.9 | 0.0 | — | — | 0.0 | — |
| MECL | 71.1 | — | 71.1 | — | — | — | — | — |
| CO | 0.5 | — | 0.5 | — | — | — | — | — |
| Mass Flow KG/HR | 28502 | 100001 | 21366 | 8000 | 99983 | 18 | 7154 | 846 |
| Volume Flow CUM/HR | 35.43 | 96.94 | 26.26 | 1614.46 | 110.50 | 0.02 | 7.83 | 0.90 |
| Density KG/CUM | 80.5 | 1032 | 756 | 4.96 | 905 | 1032 | 913 | 939 |
| Temperature C | 65.2 | 79.9 | 66.0 | 137.7 | 207.3 | 80.0 | 89.4 | 120.1 |
| Pressure BAR | 6.00 | 4.00 | 1.50 | 1.82 | 1.94 | 3.00 | 1.01 | 4.05 |

TABLE III

| Phase | Stream | | | | | | | |
|---|---|---|---|---|---|---|---|---|
| | 1 LIQUID | 2 LIQUID | 3 LIQUID | 4 VAPOR | 5 LIQUID | 6 LIQUID | 7 LIQUID | 8 LIQUID |
| Mass Flow KG/HR | | | | | | | | |
| CO2 | 78.0 | — | 78.0 | — | — | — | — | — |
| MEOH | 20019.6 | — | 20019.6 | 0.0 | — | — | 0.0 | — |
| DMC | 7782.9 | 342.3 | 652.8 | 7697.4 | 342.3 | — | 7130.1 | 567.3 |
| ANISOLE | — | 30000.0 | 0.5 | 301.4 | 29928.6 | 71.4 | 71.0 | 230.4 |
| H20 | 1.0 | 0.3 | 0.0 | 1.1 | 0.3 | — | 1.0 | 0.1 |
| DME | 50.6 | — | 50.6 | — | — | — | — | — |
| METHYLAL | 497.9 | — | 497.9 | 0.0 | — | — | 0.0 | — |
| MECL | 71.1 | — | 71.1 | — | — | — | — | — |
| CO | 0.5 | — | 0.5 | — | — | — | — | — |
| Mass Flow KG/HR | 28502 | 30343 | 21371 | 8000 | 30271 | 71 | 7202 | 798 |
| Volume Flow CUM/HR | 35.43 | 32.35 | 28.27 | 965.21 | 37.35 | 0.08 | 7.60 | 0.87 |
| Density KG/CUM | 805 | 938 | 756 | 8.29 | 810 | 938 | 947 | 913 |
| Temperature C | 65.2 | 79.9 | 66.0 | 131.8 | 195.9 | 80.0 | 65.0 | 97.8 |
| Pressure BAR | 6.00 | 4.00 | 2.86 | 2.91 | 2.93 | 3.00 | 1.01 | 3.04 |

Example 4

In this example, column A is a column having 45 theoretical stages, including reboiler and condenser. The extractive distillation agent is anisole. Numbered from the top, the condenser is stage 1. The feed, stream 1, is introduced at stage 24. The extractive distillation agent feed, stream 2, is introduced at stage 10, and the side stream, stream 4, is removed at stage 34. The top pressure is 1.5 bar, the molar reflux ratio is 1.8 and the molar boilup ratio is 6.75.

Column B is a column having 6 theoretical stages, including condenser. The top pressure is atmospheric, the molar reflux ratio is 0.18, and the mass ratio of distillate to feed is 0.90.

The results of this simulation are set forth in Table IV.

TABLE IV

| Phase | Stream | | | | | | | |
|---|---|---|---|---|---|---|---|---|
| | 1 LIQUID | 2 LIQUID | 3 LIQUID | 4 VAPOR | 5 LIQUID | 6 LIQUID | 7 LIQUID | 8 LIQUID |
| Mass Flow KG/HR | | | | | | | | |
| CO2 | 78.0 | — | 78.0 | — | — | — | — | — |
| MEOH | 20019.6 | — | 20019.2 | 0.4 | — | — | 0.4 | 0.0 |
| DMC | 7782.9 | 254.0 | 697.2 | 7745.1 | 254.0 | — | 7085.7 | 659.4 |
| ANISOLE | — | 30000.0 | 0.7 | 253.3 | 29929.1 | 70.9 | 70.1 | 183.2 |
| H20 | 1.0 | 0.6 | 0.0 | 1.1 | 0.6 | — | 1.0 | 0.1 |
| DME | 50.6 | — | 50.6 | — | — | — | — | — |
| METHYLAL | 497.9 | — | 497.9 | 0.0 | — | — | 0.0 | — |
| MECL | 71.1 | — | 71.1 | — | — | — | — | — |
| CO | 0.5 | — | 0.5 | — | — | — | — | — |
| Mass Flow K/HR | 28502 | 30255 | 21415 | 8000 | 30184 | 71 | 7157 | 843 |
| Volume Flow CUM/HR | 35.43 | 32.26 | 28.31 | 1501.89 | 36.27 | 0.08 | 7.56 | 0.92 |
| Density KG/CUM | 805 | 938 | 756 | 5.33 | 832 | 938 | 947 | 913 |
| Temperature C | 65.2 | 79.9 | 66.0 | 113.9 | 178.0 | 80.0 | 65.0 | 95.7 |
| Pressure BAR | 6.00 | 4.00 | 1.50 | 1.82 | 1.94 | 3.00 | 1.01 | 3.04 |

What is claimed is:

1. A method for separating dimethyl carbonate and methanol from a mixture comprising dimethyl carbonate and methanol in a single distillation column said column having a number of theoretical stages, said method comprising the steps of:

A) introducing a feed stream comprising dimethyl carbonate and methanol and a second stream comprising an extractive distillation agent into the distillation column, said second stream and said feed stream comprising dimethyl carbonate and methanol having a mass ratio, said mass ratio being in a range from about 0.1 to 1 to about 10 to 1, the feed stream comprising dimethyl carbonate and methanol being fed into the extractive distillation column below the second stream, the extractive distillation agent selected from the group consisting of an aromatic hydroxy compound, an alkyl aryl ether, a dialkyl carbonate, an alkyl aryl carbonate, a diaryl carbonate, an alkylene carbonate and an alicyclic alcohol, said extractive distillation agent not forming an azeotrope with methanol or dimethyl carbonate, and having a higher boiling point than both methanol and dimethyl carbonate;

B) distilling the dimethyl carbonate and methanol in the presence of the extractive distillation agent to provide in the distillation column a distillate having vapor mass fractions of the components methanol, dimethyl carbonate and extractive distillation agent; and C) removing an overhead product stream, a side product stream, and a bottom product stream from the distillation column, the overhead product stream comprising primarily methanol, the side product stream comprising primarily dimethyl carbonate and the bottom product stream comprising primarily the extractive distillation agent, said side product stream being removed at a point in said distillation column wherein the vapor mass fractions of methanol, dimethyl carbonate and extractive distillation agent are a function of the number of theoretical stages present.

2. The method of claim 1, further wherein the side product stream is removed at a point in the distillation column where the vapor mass fraction of the dimethyl carbonate in the column is at or near a maximum.

3. The method of claim 1, further comprising the step of recycling the bottom product stream to the second stream.

4. The method of claim 1, further comprising the step of feeding an extractive makeup stream to the second stream.

5. The method of claim 1, wherein the extractive distillation agent is phenol.

6. The method of claim 5, wherein the mass ratio of the second stream to the feed stream comprising dimethyl carbonate and methanol is about 2:1 to about 4:1.

7. The method of claim 1, wherein the extractive distillation agent is anisole.

8. The method of claim 7, wherein the mass ratio of the second stream to the feed stream comprising dimethyl carbonate and methanol is from about 0.5:1 to about 2:1.

9. The method of claim 1, wherein the mass ratio of the second stream to the feed stream comprising dimethyl carbonate and methanol is from about 2:1 to about 4:1.

10. The method of claim 1, wherein the side stream is removed at a pressure of from 1 to 10 bar.

11. The method of claim 1, further comprising the step of feeding the side product stream comprising primarily dimethyl carbonate to a side rectification column having a distillation zone, distilling the dimethyl carbonate to remove impurities from the dimethyl carbonate, and removing from the side rectification column a product liquid stream comprising dimethyl carbonate having a purity greater than the side product stream.

12. The method of claim 1, wherein steps A) through C) are conducted simultaneously.

* * * * *